United States Patent

Sentmanat

(10) Patent No.: US 6,666,073 B2
(45) Date of Patent: Dec. 23, 2003

(54) APPARATUS FOR PROCESS LINE TESTING

(75) Inventor: Martin Lamar Sentmanat, Akron, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 10/387,271

(22) Filed: Mar. 12, 2003

(65) Prior Publication Data

US 2003/0171849 A1 Sep. 11, 2003

Related U.S. Application Data

(62) Division of application No. 09/734,348, filed on Dec. 11, 2000.

(51) Int. Cl.$^7$ .......................... G01N 11/10; G01N 11/14
(52) U.S. Cl. .................... 73/54.37; 73/54.39; 73/54.34; 73/54.28
(58) Field of Search ............................. 73/54.37, 54.39, 73/54.34, 54.28

(56) References Cited

U.S. PATENT DOCUMENTS

| | | | |
|---|---|---|---|
| 4,468,953 A | 9/1984 | Garritano ........................ 73/60 |
| 4,570,478 A | 2/1986 | Soong ........................ 73/54.39 |
| 4,571,989 A * | 2/1986 | Dealy ........................ 73/54.39 |
| 4,643,020 A * | 2/1987 | Heinz ......................... 73/54.27 |
| 4,667,519 A | 5/1987 | Burg et al. ..................... 73/815 |
| 4,817,416 A | 4/1989 | Blanch et al. ............. 73/54.04 |
| 5,078,007 A | 1/1992 | Tadros ........................ 73/54.14 |
| 5,253,513 A | 10/1993 | Van Arsdale et al. ...... 73/54.41 |
| 5,360,549 A | 11/1994 | Mouche et al. ............. 210/101 |
| 5,708,197 A | 1/1998 | Todd et al. ................. 73/54.28 |
| 5,763,794 A | 6/1998 | Marrelli ...................... 324/640 |
| 6,098,450 A | 8/2000 | Willenbacher et al. .... 73/54.01 |
| 6,151,557 A | 11/2000 | Broden et al. ................ 702/47 |
| 6,534,010 B2 * | 3/2003 | Sentmanat ................. 422/68.1 |
| 2002/0072123 A1 | 6/2002 | Sentmanat |

* cited by examiner

*Primary Examiner*—Hezron Williams
*Assistant Examiner*—Rodney T. Frank
(74) *Attorney, Agent, or Firm*—David L. King

(57) ABSTRACT

The invention relates to an apparatus and method for testing the properties of chemicals in a reaction flow stream. In the method, chemicals from the reaction flow stream are directed to the apparatus for testing the physical properties of the chemicals, which is an indication of the state of the chemical reaction. Data measured by the apparatus is stored in a computer, and the computer may be used to analyze the data and to control the reaction parameters based on the analysis of the data. The apparatus used for the analysis comprises a rheometer having an actuated shaft and a concentric container, wherein the shear properties of the material sampled in the apparatus are measured when the actuator shaft is oscillated within the container. Various unique configurations of the apparatus are described.

5 Claims, 6 Drawing Sheets

APPARATUS FOR PROCESS LINE TESTING

This is a Divisional of Application Ser. No. 09/734,348, filed Dec. 11, 2000, presently pending.

FIELD OF THE INVENTION

The invention relates to an in-line or on-line testing device used for analyzing the state of a chemical reaction. In a specific embodiment, the testing device is a rheometer.

BACKGROUND OF THE INVENTION

Many chemical reactions are carried out in a continuous process, because of the efficiencies inherent in continuous processing related to yield and to eliminating the need to isolate intermediate products. In continuous chemical processing, it is sometimes important, in a multi-step chemical reaction, that the reaction reach a particular stage before parameters are changed, such as the addition of chemical compounds to the reaction, changes in temperature or atmospheric conditions, and the like. In the art, the status of the chemical reaction is often measured by removing a sample of material from the reaction process line, quenching the material, i.e. stopping the process of the chemical reaction, and analyzing the chemicals in the sample. The chemicals in the sample at that particular point define the status of the chemical reaction at that point, and tells the technician whether the reaction is proceeding as planned, and whether conditions are right for adding additional chemical reactants, or for changing the temperature or other parameters in the processing line.

A common means for determining the state of reaction of a process is to measure certain physical properties of the compound mixture which are a reflection of the nature of the material. Most chemicals, in a fluid state, exhibit rheological (flow) properties that are a function of the molecular size and structure of the material. For small chemical molecules with simple structure, the rheological properties of the material are fluid-like, independent of the rate and size of the applied deformation, and can be characterized in terms of a simple viscometric function such as a Newtonian viscosity. As molecular size and structure increases, a material's Theological properties become more complex and are dependent on the size and rate of the applied deformation. Polymeric materials are comprised of very long molecules and exhibit viscous (fluid-like) as well as elastic (solid-like) behavior, known to those skilled in the art as viscoelasticity. Although characterizing the viscosity of a polymer can be descriptive of its molecular size, a viscoelastic characterization which is more sensitive to molecular structure is required since a viscometric function is not descriptive of the elastic nature of the material. A more thorough treatment for describing the molecular mechanisms underlying the viscoelastic rheological behavior of polymeric fluids can be found in "Viscoelastic Properties of Polymers" by J. Ferry, Third Edition, John Wiley & Sons, New York (1980).

In the chemical processing art, it is a continuing goal to completely automate the processing line. By that, it is meant that if analysis of the chemical reaction stream can be made at critical points, and the data from those critical points is fed into a computer, the computer can use the information to know when to adjust the reaction conditions as necessary, to assure that the chemical reaction goes as planned, which will improve the efficiency and yield of the chemical process. The nature of the analyzing equipment used at the critical points depends on the nature of the chemical reaction and the kind of data that will be most useful in analyzing the status of the chemical reaction. Since a chemical processing line is sometimes used for preparing more than one kind of chemical, and the materials used in the chemical processing line will change depending on the reaction, it is desirable that the analyzing equipment used be useful for a broad spectrum of chemical reactions.

It is an object of the present invention to provide a method and apparatus for analyzing the chemical or physical properties of a fluid in a reaction flow stream.

Other objects of the invention will be apparent from the following description and claims.

DESCRIPTION OF PRIOR ART

Various apparati have been developed for the use of on-line monitoring of a chemical process, most of which involve taking a side stream and pumping it through a capillary, slit, or rotating cylinder type of rheometer. These types of rheometers, however, typically provide only a viscometric and not a viscoelastic characterization of a fluid.

U.S. Pat. No. 4,468,953 (Garritano) describes an on-line concentric cylinder rotational rheometer for determining the vicoelastic properties of a fluid sampled from a process stream. The sampled fluid is introduced into the annular region of the concentric cylinders by means of a gear pump. The outer cylinder is made to oscillate about its axis of symmetry by means of a drive shaft and motor assembly, and the resultant torque on the inner cylinder is measured by means of a torsion tube assembly that is hermetically sealed. Flow into the rheometer is distributed uniformly through the annulus so that the introduction of fresh sample flushes the previous fluid sample out of the annulus. In order to allow free oscillation of the outer cylinder, however, the drive shaft requires the use of seals that are exposed to the thermal, chemical, and abrasive properties of the fluid. These seals require regular maintenance of the device and provide a possible source of failure during operation that could expose the surrounding environment to the hazards of the fluids being tested.

U.S. Pat. No. 4,643,020 (Heinz) describes a concentric cylinder process rheometer for characterizing the viscoleastic properties of a fluid that can be used either on-line or in the process stream. The sensing device consists of three concentric, thin-walled cylinders, the middle cylinder of which is made to oscillate about its axis of symmetry. The motion of the drive cylinder applies a shear to the fluid in the adjacent annular regions which causes a resultant torque on the drive cylinder that is measured on the drive shaft by means of a torsion tube and sensor assembly. Flexible bellows are used to seal the pivoting drive shaft from the fluid environment. Sample flushing out of the rheometer is uncontrolled, however, and the design does not allow for metered fluid flow into and out of the adjacent annuli to permit fresh sampling into the rheometer.

SUMMARY OF THE INVENTION

An apparatus for measuring the state of a chemical reaction in a process line comprises: (a) a cell of fixed volume for sampling and collecting material from a chemical process stream, and (b) a rheometer in which a portion of the sampled material is confined within a shearing gap where a controlled shear deformation is applied to the material and the response from the sheared material is measured.

In the illustrated embodiment, the rheometer cell is located external to the process stream, and material is allowed to enter and exit the cell by means of flow conduits and valves. The shearing gap is defined by the annulus of two substantially parallel concentric cylinder shafts. The inner cylinder moves axially in oscillation along its primary axis and is attached to a means of resolving (measuring) the physical material response to the applied deformation, in this case a force transducer.

Also provided is a method for measuring the flow response of fluids in a shear rheometer comprising the steps of a) providing an apparatus for measuring the rate of shear flow of fluids comprising a drive shaft mounted external to the rheometer cell wherein the drive shaft is connected to a moving cylinder that defines the applied shear deformation, b) confining a portion of sampled material within the defined shear gap, c) causing the material confined within the defined gap to be sheared by the motion of the moving cylinder, and d) measuring the physical response created by the shearing of the sample.

An oscillating shear deformation is applied in order to assess the in-phase and out-of-phase physical responses to the applied deformation that are a reflection of the viscoelastic nature of a polymeric fluid. A step shear deformation may also be applied to the fluid in the gap, as in the case of a shear stress relaxation experiment. The shear deformation may also be applied such that the rate of fluid deformation in the shear gap is steady, as in the case of a viscometric flow characterization.

The rheometer provides a method for measuring the viscoelastic rheological properties of a fluid chemical that are a reflection of the state of chemical reaction of that chemical based on its molecular size and structure.

In an alternative embodiment, an apparatus 110 for inline testing of the properties of a fluid in a reaction flow stream comprises a container 122, consisting of container ends 122B, 122C and ring 122A connected to each other by bellows 120. An actuator shaft 124 within container 122 is connected to a shearing ring 126, the actuator shaft 124 being adapted to move shearing ring 126 within the container 122. A force transducer 128 is associated with the ring 122A for measuring torque forces on ring 122A.

The apparatus 110 has a shearing gap 116 which separates ring 122A and shearing ring 126 when shearing ring 126 is positioned within container 122 for obtaining test data. Shearing ring 126 has a cross-sectional shape which includes recirculation gaps 118. Apparatus 110 is adapted to be connected to a reaction flow stream by a tap line whereby a sample enters apparatus 110 through a first end 122B through portal 112, and exits apparatus 110 through portal 112A in second end 122C.

DETAILED DESCRIPTION OF THE INVENTION

Most chemicals, in a fluid state, exhibit viscous properties. Polymeric materials exhibit viscous (fluid-like) as well as elastic (solid-like) behavior, known to those skilled in the art as viscoelastacity. Elastomers exhibit greater elastic properties than other polymers. In the conception of the invention, the inventors proposed to use the known viscous nature of a fluid as an indicator of the contents of the fluid.

Figure 1:
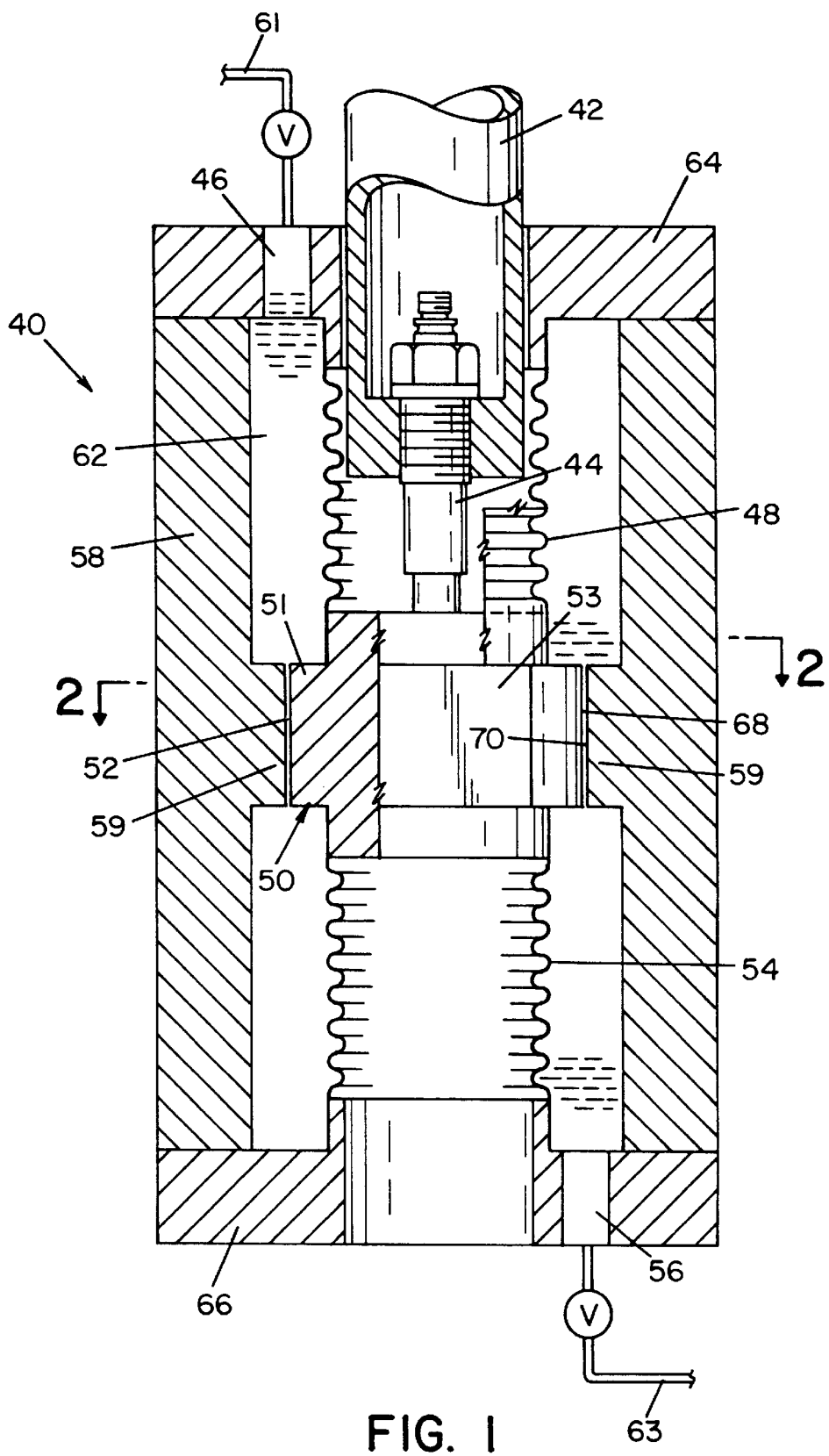
FIG. 1 illustrates a cutaway side view of an apparatus of the invention.
Figure 2:
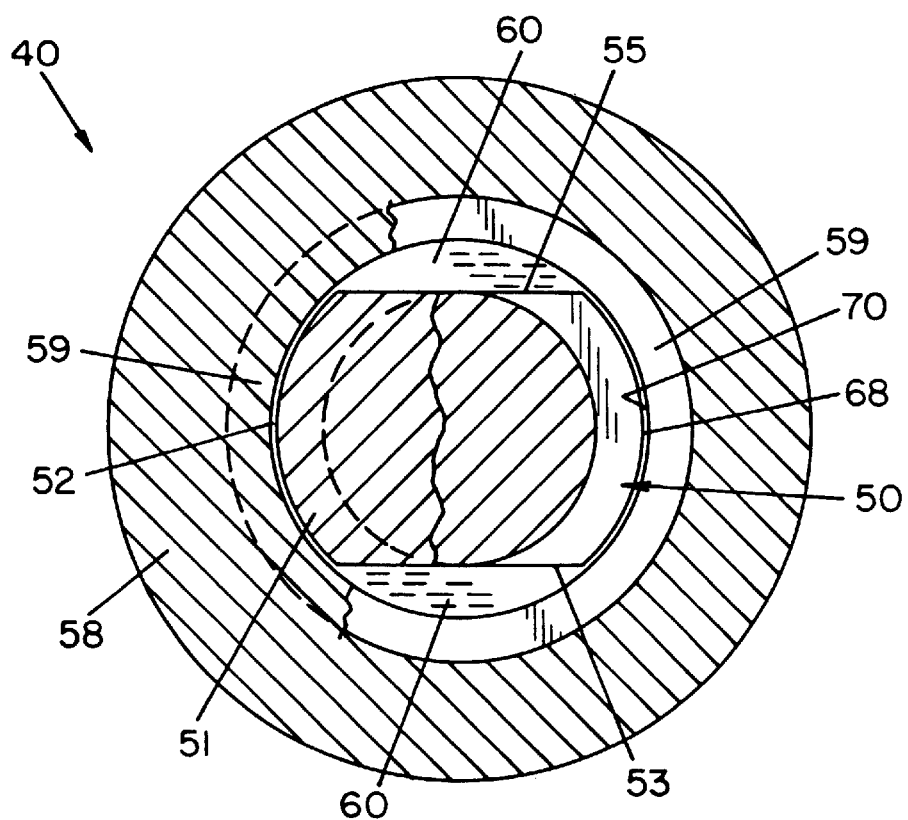
FIG. 2 illustrates a cross sectional top view taken along line 2—2 of the apparatus of FIG. 1.
Figure 3:
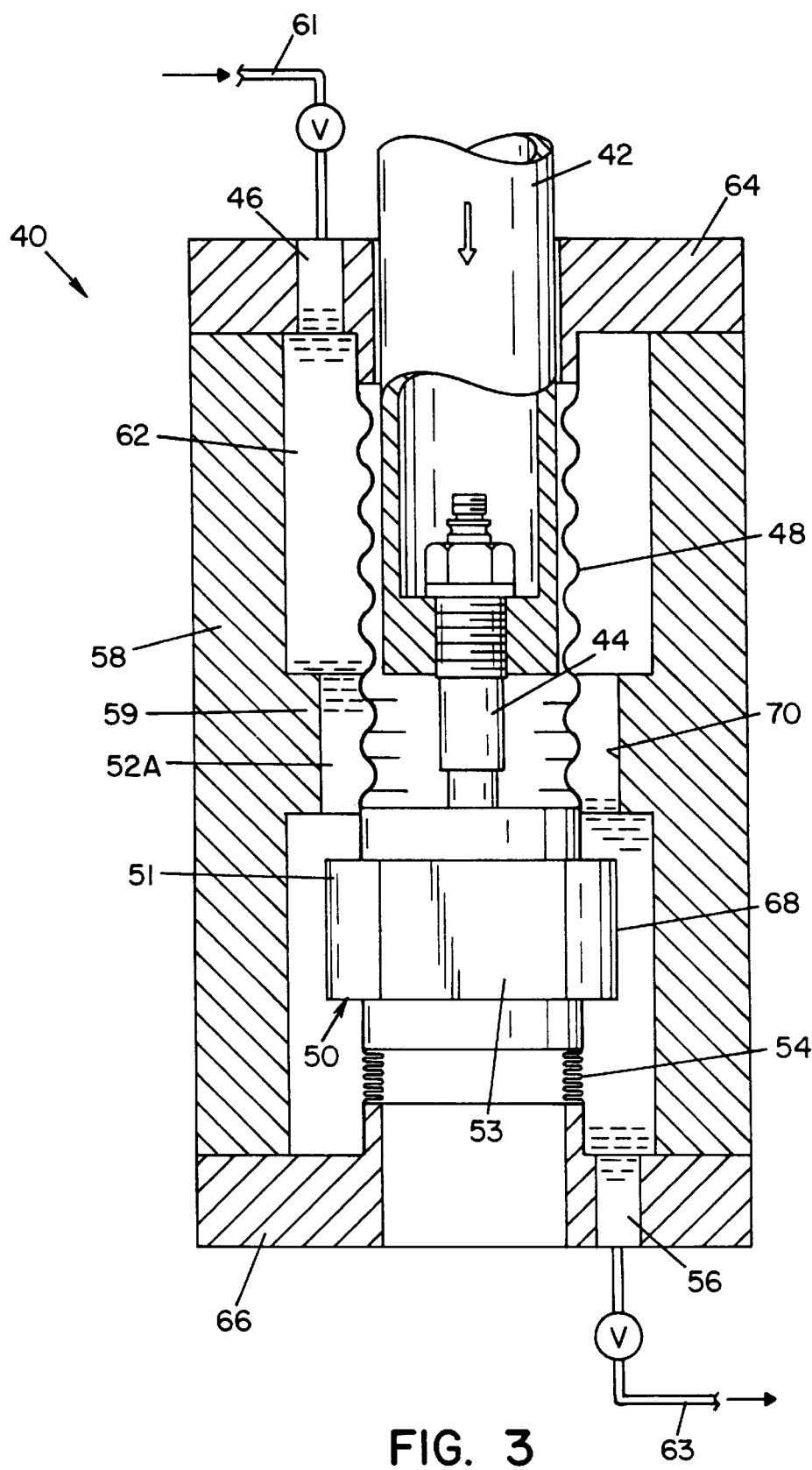
FIG. 3 illustrates the apparatus of FIG. 1 in an open condition.

With reference now to FIGS. 1–3, an apparatus 40 which may be used in the invention is illustrated. The apparatus 40 comprises a sample chamber which is enclosed in sample container walls 58 which are sealed by ends 64 and 66. An entry port 46 for the sample is provided in end 64, and an exit port 56 for the sample is provided in end 66. Accordingly, the sample must pass through entry port 46 into sample reservoir 62.

Apparatus 40 is designed to be attached to a tap line 61 which is connected to the chemical processing line, whereby the tap line may be opened to obtain a sample. After data is obtained, the sample may be returned through another tap line 63 to the chemical processing line through exit port 56, or the sample may be discarded, or collected for additional testing.

In apparatus 40, the viscoelastic properties of the sample are measured by the shear of the sample, by trapping the sample in shearing gap 52 between shearing block 50 and step 59 in sample container wall 58. To obtain a measurement, an actuator shaft 42 causes shearing block 50 to move back and forth in the proximity of step 59, and the shear on the sample caused by the motion of a shearing block 50 in shearing gap 52 is measured using force transducer 44. Bellows 48, 54 facilitate the back-and-forth motion of shearing block 50, while sealing the internal components of the apparatus from the chemicals of the sample.

With reference specifically to FIGS. 1 and 2, when measurements are being taken on a sample, step 59 of container wall 58, and outcropping 51 of shearing block 50 are separated by shearing gap 52 at opposed surfaces 68 and 70 of shearing block 50 and of step 59, respectively. The viscoelastic properties of the sample dictate the shear, i.e. the force of resistance measured by force transducer 44. In the illustrated embodiment, the cross section of shearing block 50 is part of a circle which fits within the circle of step 59 in circular container walls 58. It should be apparent to those skilled in the art that other geometric configurations can be used for obtaining the shear properties of the sample.

Shearing block 50 is made with flat sides 53, 55, which create a recirculation gap 60 when shearing block 50 is disposed in the proximity of step 59 of container walls 58. Recirculation gap 60 permits motion of the sample into and out of sample reservoir 62 so that hydraulic pressures in the sample container do not interfere with the shear data that is to be obtained. Those skilled in the art will recognize that sample reservoir 62 need not be completely filled with sample, i.e. an air gap can be provided, as long as the shearing gap 52 is completely filled when data is being obtained on a sample.

With reference now to FIG. 3, when data on a sample has been obtained, and it is desired to flush the sample from sample container 40, shear block 50 is extended by shaft 42 into a position wherein shear block 50 is removed from the proximity of step 59 of container walls 58. Bellows 48 and 54 facilitate this motion wherein, in the illustrated embodiment, bellows 48 are extended, and bellows 54 are compressed, while the seal between the internal components of the apparatus and the chemicals being tested is maintained.

Those skilled in the art will recognize that instead of extending shear block 50 toward sample exit port 56, it is possible to build the apparatus so that shear block 50 is retracted toward entry port 46 when shear block 50 is removed from the proximity of step 59 in container walls 58.

As illustrated in FIG. 3, when the shaft actuator (not shown) is activated, shearing gap 52 no longer exists, and a resampling gap 52A is created between step 59 and shearing block 50. Resampling gap 52A permits flushing of the sample from the sampling device, and replacing the measured sample with a new sample of material that is to be measured.

In the method of the invention, when it is desired that data be obtained from a sample using apparatus 40, the apparatus is retained in a configuration as illustrated in FIG. 3, and sample entry port 46 is opened and sample exit port 56 is closed so that sample is drawn into sample reservoir 62. When sufficient sample has been received into sample reservoir 62, sample entry port 46 is closed, isolating the sample from the reaction processing line. Thereafter, as illustrated in FIG. 1, the shaft actuator is activated to draw shearing block 50 into the proximity of step 59 in container walls 58, creating a shearing gap 52. Shaft 42 is then actuated to move shearing block 50 in a back and forth motion to create a shear in the sample between face 68 of shearing block 50 and face 70 of step 59. Force transducer 44 measures the resistance force created by the sample, which is an indication of the sample's viscoelastic properties.

When the data is obtained, the collected data can be transferred to a computer, and the information will indicate the status of the chemical reaction in the chemical processing line, i.e. the state of the completion of the chemical reaction. This information will be used by the computer to maintain or change the flow rate of chemicals through the chemical processing line, maintain or change the temperature in the chemical processing line, or activate other parameters that will affect the rate of the reaction or to maintain the rate of the reaction.

It has been found, in creating the apparatus shown in FIGS. 1–3, that materials are not yet available that make possible the miniaturization of the hermetically sealed apparatus on the scale desired by the inventor. With materials available, the inventor estimates that the sample size for the apparatus of FIGS. 1–3 will need to be several liters due to the size and sensitivity requirements of bellows 48, 54. Although usable in large reaction lines, such as those seen in refineries and synthetic rubber manufacturing, the inventor sees a need for such testing on a smaller sampling scale.

Figure 4:
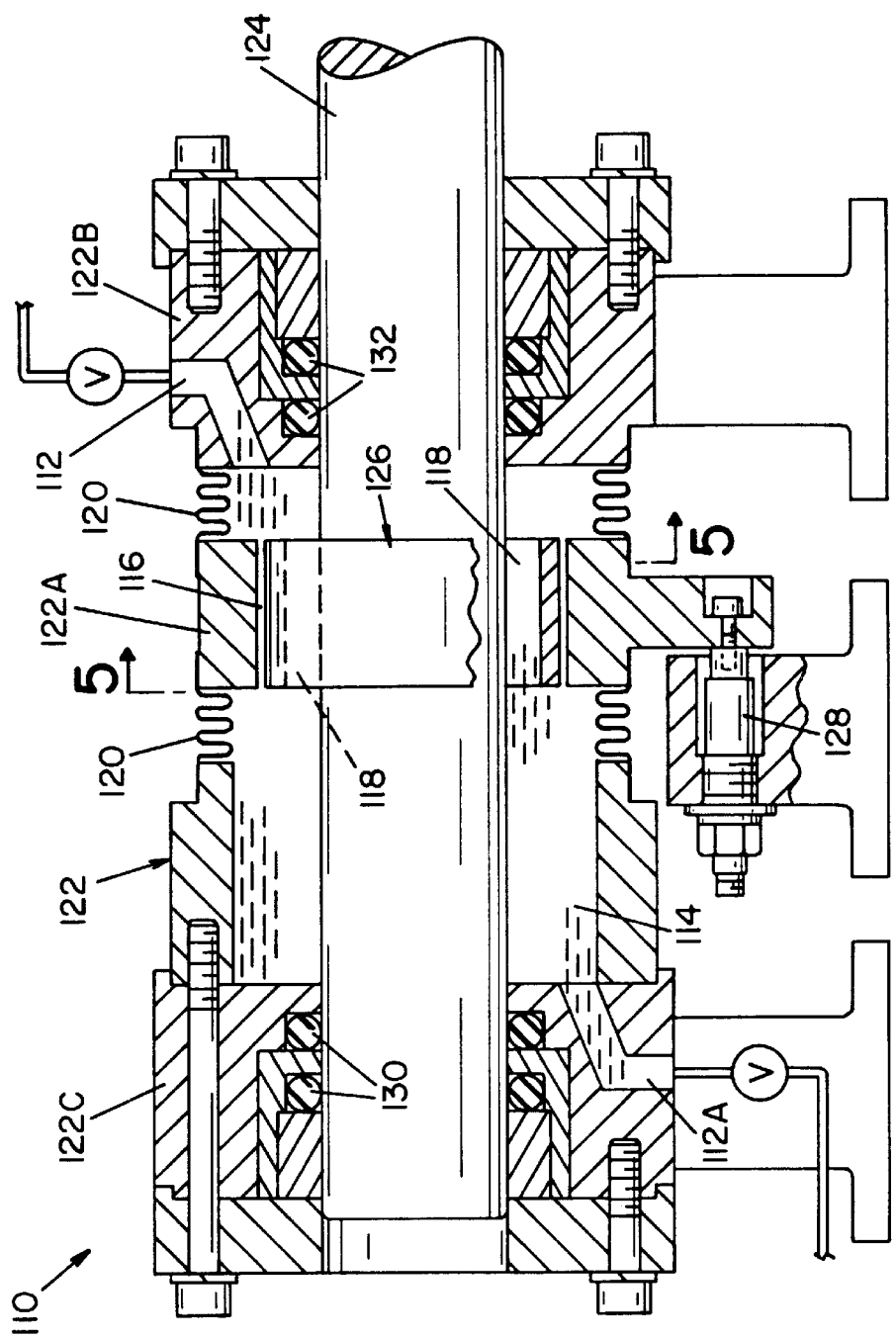
FIG. 4 illustrates a cutaway side view of an alternative apparatus of the invention.
Figure 5:
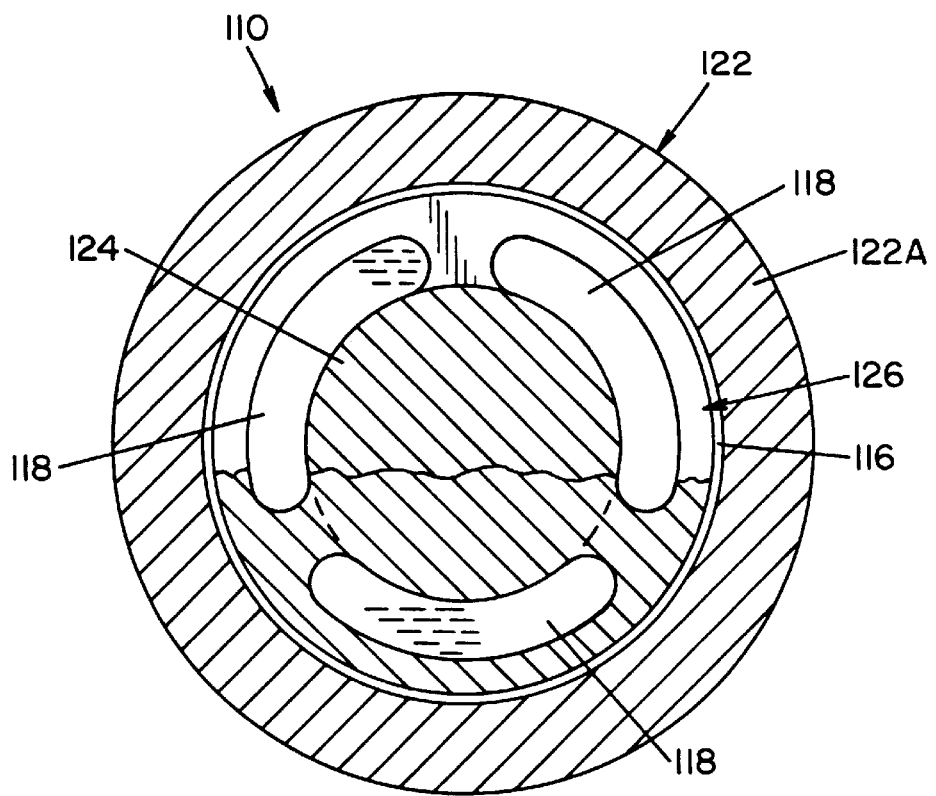
FIG. 5 illustrates a cross sectional top view taken along line 5—5 of the apparatus of FIG. 4.
Figure 6:
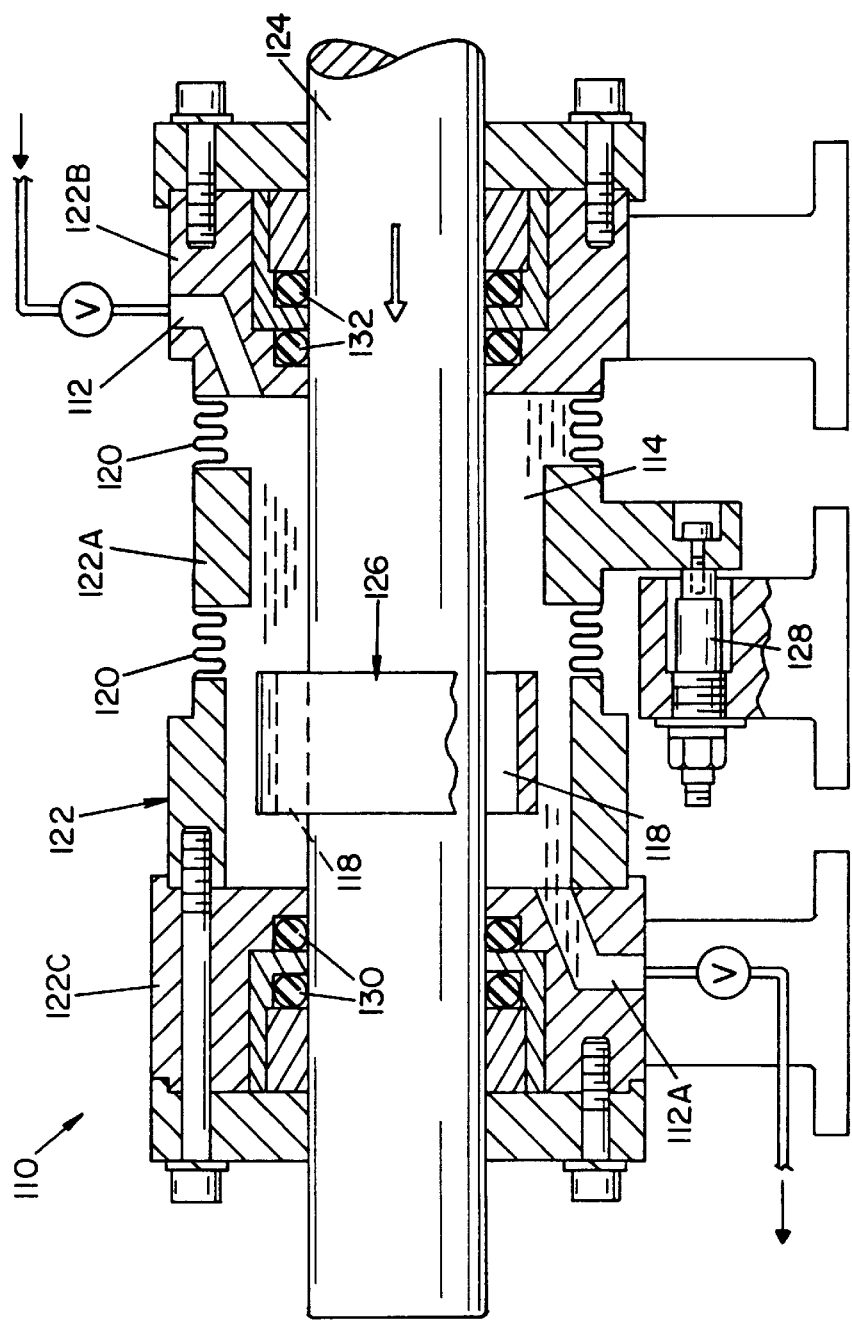
FIG. 6 illustrates the apparatus of FIG. 4 in an open condition.

Accordingly, in an alternative embodiment, as illustrated in FIGS. 4–6, the same basic principles are used in an embodiment in apparatus 110 wherein actuator shaft 124, having a shearing ring 126 is oscillated back and forth in a container 122 which comprises a first end 122B, a second end 122C, and a ring 122A which are connected to each other by bellows 120. The alternative apparatus shown in FIGS. 4–6 operates on the same principles as the apparatus shown in FIGS. 1–3 in that the shearing force of a sample trapped within shearing gap 116 is measured when shaft 124 is oscillated within container 122.

The apparatus 110 has a shearing gap 116 which separates ring 122A and shearing ring 126 when shearing ring 126 is positioned within container 122 for obtaining test data. Shearing ring 126 has a cross-sectional shape which includes recirculation gaps 118. Apparatus 110 is adapted to be connected to a reaction flow stream by a tap line whereby a sample enters apparatus 110 through a first end 122B through portal 112, and exits apparatus 110 through portal 112A in second end 122C.

In the embodiment of FIGS. 4–6, bellows 120 are very stiff, and ring 122A is stationary, or substantially stationary, within container 122 when a shearing stress of a sample acts over the internal surface of ring 122A as shaft 124 is oscillated. Force transducer 128, which is associated with ring 122A, is capable of measuring forces that are applied to ring 122A by the shearing force of the sample in shearing gap 116. Transducer 128 is capable of measuring forces in the range of 0.001 to 500 Newtons. Those skilled in the art will recognize that alternatively the axial deflection of ring 122A may also be measured as a means of resolving the physical response of the material to the applied shear deformation. In such a case, the measured axial deflection of the ring 122A is governed by the spring rate of the attached bellows.

In the illustrated embodiment, bellows 120 are of precision construction and made of nickel which has a thickness of 0.1 mm.

In the construction of apparatus 110, seals 132 are provided in first end 122B of container 122, and seals 130 are contained in second end 122C of container 122 to contain a sample within sample cavity 114 of container 122.

In the illustrated embodiment, seals 130, 132 comprise spring energized PTFE seals from Bal Seal Engineering Company.

The transducer 128 is the same as that illustrated with respect to FIGS. 1–3.

Similar to what was described with regard to the apparatus described in FIGS. 1–3, and with reference specifically to FIG. 6, when it is desired to collect a sample in apparatus 110, a valve and tap line leading from a reaction flow line is opened to sample entry port 112, and sample exit port 112A is closed to permit entry and containment of the sample in sample chamber 114. When the desired volume of sample has entered sample chamber 114, the sample entry port 112 is closed to isolate the sample and sample chamber 114 from the reaction flow line, and shaft 124 is activated about 4 centimeters so that shearing ring 126 is opposite center ring 122A as is illustrated in FIG. 4. Shaft 124 is oscillated using a linear motor stage (not shown) provided by Aerotech, Inc.

The linear motor is one factor that makes possible the small size of the apparatus shown in FIGS. 4–6. The ALS20000 series linear motor stage by Aerotech, Inc. has a stroke range of 10 cm, which is sufficient to move shearing ring 126 clear of center ring 122A when the apparatus is open to a new sample as shown in FIG. 6. The motor is also capable of oscillating shaft 124 at frequencies greater than 100 Hz, which is suitable for creating a dynamic shear in a sample being tested.

The sheared sample in shear gap 116 between shearing ring 126 and ring 122A applies a shear stress over the internal surface of ring 122A, which is measured as a dynamic axial load by force transducer 128. After the data is collected on a sample, sample exit port 112A is opened, and the sample is permitted to return to the reaction flow line, or is collected for further testing as desired.

The data can be collected and used as is illustrated with respect to the apparatus described in FIGS. 1–3.

While the invention has been specifically illustrated and described, those skilled in the art will recognize that the invention can be variously modified and practiced without departing from the spirit of the invention.

What is claimed is:

1. An apparatus for inline testing of properties of a fluid in a reaction flow stream comprising
   (a) container walls connected to first and second container ends,
   (b) an actuator shaft associated with a first end, said actuator shaft being connected to a shear block and being adapted for moving a shear block within said container walls, and
   (c) a force transducer 44 being associated with said actuator shaft for measuring torque forces on said actuator shaft; and
   (d) an outcropping in container walls and a step on shearing block, separated by shearing gap, said outcropping and said step being adapted to be in close proximity to one another when shearing block is positioned within apparatus for obtaining test data.

2. The apparatus of claim 1 wherein shearing block has a cross-sectional shape different from the cross-sectional shape of outcropping, wherein recirculation gaps are provided between outcropping and step when apparatus is in testing mode.

3. The apparatus of claim 1 wherein the actuator shaft and transducer 44 are protected from a sample by bellows, said bellows permitting movement of actuator shaft within apparatus.

4. The apparatus of claim 1 which is adapted to be connected to a reaction flow stream by a tap line whereby a sample enters apparatus through said first end through portal and exits apparatus through portal at said second end.

5. The apparatus of claim 4 wherein stopping means are provided for isolating a sample from a reaction flow stream by stopping sample flow through said portals when data is being obtained on said sample.

* * * * *